United States Patent [19]

Yang et al.

[11] Patent Number: 5,719,272
[45] Date of Patent: Feb. 17, 1998

[54] 2'-PROTECTED 3'-DIMETHYLAMINE, 9-ETHEROXIME ERYTHROMYCIN A DERIVATIVES

[75] Inventors: Chengxi Yang, Glenview; Hemantkumar H. Patel, Waukegan; Yi-Yin Ku, Buffalo Grove; Jih-Hua Liu, Green Oaks, all of Ill.

[73] Assignee: Abbott Laboratories, Abbott Park, Ill.

[21] Appl. No.: 627,795

[22] Filed: Apr. 2, 1996

[51] Int. Cl.⁶ .................. C07H 1/00; C07H 17/08
[52] U.S. Cl. .................. 536/7.4; 536/7.2; 536/18.5; 536/18.6
[58] Field of Search .................. 536/7.2, 7.4, 18.5, 536/18.6

[56] References Cited

U.S. PATENT DOCUMENTS 4,670,549  6/1987  Morimoto et al. .................. 536/7.4
5,350,839  9/1994  Asaka et al. .................. 536/7.4

*Primary Examiner*—Elli Peselev
*Attorney, Agent, or Firm*—Mona Anand; Thomas D. Brainard

[57] ABSTRACT

A process of preparing a 6-O-methyl erythromycin A derivative using a 2'-protected, 9-etheroxime erythromycin A intermediate is provided. A preferred protecting group for the 2'-position is acetyl. 2'-protected, 9-etheroxime erythromycin A derivatives are also provided. Also disclosed is a method for inhibiting quaternary salt formation at the 3' amine without the need for 3'N-protecting groups.

13 Claims, 4 Drawing Sheets

2'-PROTECTED 3'-DIMETHYLAMINE, 9-ETHEROXIME ERYTHROMYCIN A DERIVATIVES

TECHNICAL FIELD OF THE INVENTION

The field of the invention is erythromycin derivatives. More particularly, the present invention pertains to 2'-protected, 3'-dimethylamine, 9-oxime erythromycin A derivatives and their use in the production of 6-O-alkyl erythromycin A.

BACKGROUND OF THE INVENTION

6-O-methylerythromycin A (clarithromycin), shown below, is a potent macrolide antibiotic (U.S. Pat. No. 4,331, 803).

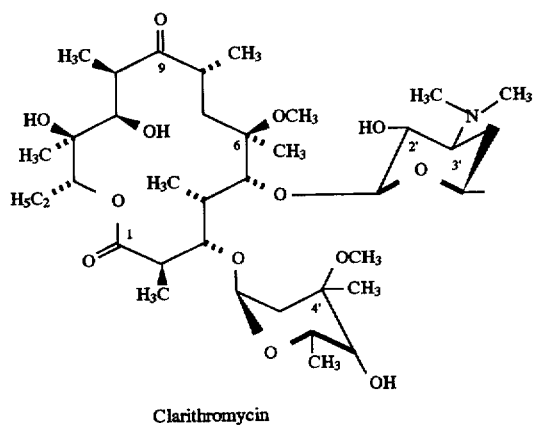

Clarithromycin

A variety of means for preparing 6-O-methylerythromycin A have been described. 6-O-methylerythromycin A can be prepared by methylating a 2'-O-3'-N-dibenzyloxycarbonyl-des-N-methyl derivative of erythromycin A (U.S. Pat. No. 4,331,803). 6-O-methylerythromycin A can also be made from 9-oxime erythromycin A derivatives (See, e.g., U.S. Pat. Nos. 5,274, 085; 4,680386; 4,668776; 4,670,549 and 4,672,109 and European Patent Application 0260938 A2).

In those reports relating to 9-oxime erythromycin A derivatives, the oxime is protected during methylation with a 2-alkenyl group (U.S. Pat. Nos. 4,670,549 and 4,668,776), a benzyl or substituted benzyl group (U.S. Pat. Nos. 4,680, 386, and 4,670,549) or a moiety selected from the group consisting of lower alkyl, substituted alkyl, lower alkenyl, aryl substituted methyl, substituted oxalkyl, and substituted thiomethyl (U.S. Pat. No. 4,672,109).

There are drawbacks to the existing methods for producing 6-O-methylerythromycin A. By way of example, failure to protect the 2'—OH group leads to undesired methylation of that group. Existing methods for protecting the 2'—OH group are unsatisfactory because those methods also require protection of the 3'-nitrogen. U.S. Pat. No. 4,680,386 discloses protection of the 2'—OH group with a benzyloxy carbonyl moiety. Under such circumstances, however, the 3'-nitrogen also undergoes N-demethylation followed by N-benzyloxy carbonyl formation. This 3'-N-benzyloxy carbonyl group must be deprotected following 6-O-methylation. The 3'-dimethylamino group is regenerated following 6-O-methylation by N-methylation. U.S. Pat. No. 4,670,549 discloses protection of the 2'—OH group as a benzyl or like substituent. Under these circumstances, the 3'-nitrogen group must also be protected as a quaternary salt.

This quaternary salt must be removed following 6-O-methylation to regenerate the 3'-dimethyl amino group. Deprotection of 9-oxime protected with oxyalkyls has to be carried out in harsh conditions, which lead to undesired side product formation. By way of further example, the use of benzyloxycarbonyl groups for protection of the 2'-hydroxy group (U.S. Pat. No. 4,311,803) requires large amounts of benzyl chloroformate, which is severely irritating and toxic.

There continues to be a need to provide a rapid, efficient method of producing 6-O-alkylerythromycin A that uses mild, neutral synthetic conditions. In particular, it is desirable to avoid or minimize the formation of quaternary ammonium salts at the desosamine nitrogen during the alkylation step in the production of 6-O-alkylerythromycin A derivatives.

BRIEF SUMMARY OF THE INVENTION

The present invention provides an efficient and practical method of synthesizing clarithromycin and other 6-O-alkyl analogs of erythromycin A. The synthetic process starts with a 9-O-protected oxime erythromycin A derivative, which is protected at the 2'-position with an O-protecting group to form a 2'-protected, 3'-dimethylamine, 9-O-protected oxime erythromycin A derivative and reacting the 2'-protected derivative with an alkylating agent, typically a methylating reagent, in the presence of methyl-t-butyl ether. A preferred 9-O-protected oxime is an alkylcyclohexyloxime or a halobenzyloxime. A preferred O-protecting group for the 2'-position is acetyl or benzoyl.

The present invention further provides 2'-protected, 3'-dimethylamine, 9-O-protected oxime erythromycin A derivatives used as intermediates in the production of 6-O-alkyl erythromycin A.

In yet another aspect, the invention provides a method of inhibiting the formation of quaternary ammonium salts in the preparation of 6-O-alkyl-erythromycin A compounds, said method comprising:

reacting a protected erythromycin A compound with an alkylating agent in the presence of methyl-t-butyl ether, wherein said protected erythromycin A compound includes at least a 9-oxime protection group and a 2'-hydroxyl protecting group selected from the group consisting of alkoxycarbonyl, alkoxyalkoxy-carbonyl, haloalkoxycarbonyl, unsaturated alkoxycarbonyl, substituted benzyloxycarbonyl, substituted phenoxycarbonyl, acyl and aroyl; and deprotecting the 9- and 2'-positions to give 6-O-alkyl erythromycin A.

Preferably the alkylating agent is a methylating agent, thereby producing 6-O-methylerythromycin A, clarithromycin.

While not intending to be limited by any particular theory, it is believed that the effect of methyl-t-butyl ether in the alkylation reaction controls and slows down the the rate of the alkylation reaction. The effect is to decrease quaternary salt formation even when the 3'N is unprotected, and to improve yield of the desired compound.

BRIEF DESCRIPTION OF THE DRAWINGS

In the drawings, which form a portion of the specification.

DETAILED DESCRIPTION OF THE INVENTION

Figure 1:
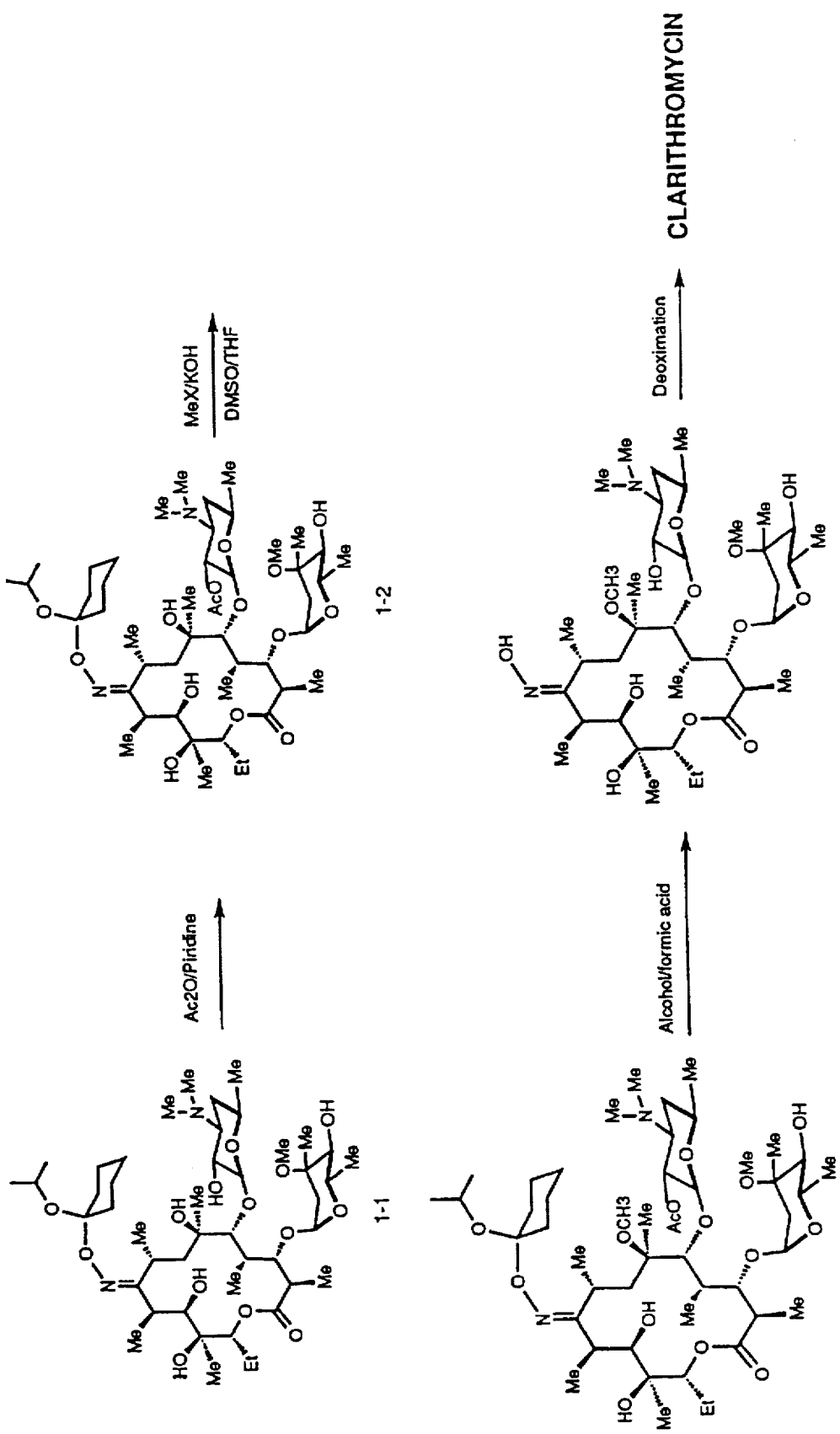
FIG. 1 shows a first embodiment of a process of preparing 6-O-methyl erythromycin A using an isopropyl cyclohexyl ketal-protecting group on the 9-oxime and an acetyl protecting group on the 2'—OH.

A number of defined terms are used herein to designate particular elements of the present invention. When so used, the following meanings are intended:

The term "alkyl" refers to saturated, straight or branched-chain hydrocarbon radicals containing between one and ten carbon atoms including, but not limited to, methyl, ethyl, propyl, isopropyl, n-butyl, tert-butyl and neopentyl. More preferably, the alkyl is limited to 1–4 carbons.

The term "alkylating agent" refers to a reagent capable of placing an alkyl group onto a nucleophilic site, including, but not limited to, alkyl halides such as methyl bromide, ethyl bromide, n-propyl bromide, methyl iodide, ethyl iodide; and n-propyl bromide; dialkyl sulfates such as dimethyl sulfate, diethyl sulfate; and di-n-propyl sulfate; and alkyl or aryl sulfonates such as methyl-p-toluenesulfonate, ethyl methanesulfonate, n-propyl methanesulfonate, and the like. The term "aryl(lower alkyl)" refers to a lower alkyl radical having appended thereto 1–3 aromatic hydrocarbon groups, as for example benzyl, diphenylbenzyl, trityl and phenylethyl.

The term "aryloxy" refers to an aromatic hydrocarbon radical which is joined to the rest of the molecule via an ether linkage (i.e., through an oxygen atom), as for example phenoxy.

The term "cycloalkyl" refers to a saturated monocyclic hydrocarbon radical having from three to eight carbon atoms in the ring and optionally substituted with between one and three additional radicals selected from among lower alkyl, halo(lower alkyl), lower alkoxy, and halogen. Examples of cycloalkyl radicals include, but are not limited to, cyclopropyl, cyclobutyl, cyclopentyl, cyclohexyl, cycloheptyl, 1-fluoro-cyclopropyl, and 2-fluorocyclopropyl.

The term "lower alkenyl" refers to a straight or branched-chain hydrocarbon radical containing between two and six carbon atoms and possessing at least one carbon-carbon double bond. Examples of lower alkenyl radicals include vinyl, allyl, 2- or 3-butenyl, 2-, 3- or 4-pentenyl, 2-, 3-, 4- or 5-hexenyl and isomeric forms thereof.

The term "lower alkoxy" refers to a lower alkyl radical which is joined to the rest of the molecule via an ether linkage (i.e., through an oxygen atom). Examples of lower alkoxy radicals include, but are not limited to, methoxy and ethoxy.

The term "lower alkyl" refers to an alkyl radical containing one to six carbon atoms including, but not limited to, methyl, ethyl, propyl, isopropyl, n-butyl, tert-butyl and neopentyl.

The term "polar aprotic solvent" refers to polar organic solvents lacking an easily removable proton, including, but not limited to, N,N-dimethylformamide, dimethyl sulfoxide, N-methyl-2-pyrrolidone, hexamethylphosphoric triamide, tetrahydrofuran, 1,2-dimethoxyethane, acetonitrile or ethyl acetate, and the like.

The term "strong alkai metal base" refers to an alkali metal base having a weak conjugate acid, including, but not limited to, sodium hydroxide, potassium hydroxide, sodium hydride, potassium hydride, potassium t-butoxide, and the like.

The term "substituted aryl(lower alkyl)" refers to an aryl(lower alkyl) residue as defined above having between one and three non-hydrogen ring substituents, each independently selected from among halogen, lower alkoxy, lower alkyl, hydroxy-substituted lower alkyl, and (lower alkyl)amino. Examples of substituted aryl(lower alkyl) radicals include 2-fluorophenylmethyl, 4-fluorophenylethyl and 2,4-difluorophenylpropyl.

The term "weak organic amine base" refers to an organic amine base having a strong conjugate acid, including, but not limited to trimethylamine, triethylamine, tripropylamine, pyridine, 2-methoxypyridine, 1-methylpyrrolidine, 1-methylpiperidine, and 1-ethylpiperidine, and the like.

In one aspect, the present invention provides a process of preparing a 6-O-alkyl derivative of erythromycin A. That process includes the steps of selectively protecting the 2'-position of a 9-O-protected oxime erythromycin A derivative and reacting that 2'-protected derivative with an alkylating agent, typically a methylating agent, in the presence of methyl-t-butyl ether.

A process of the present invention begins with a 9-oxime erythromycin A derivative. 9-Oxime erythromycin A derivatives are prepared using standard procedures well known in the art. Briefly, erythromycin A is reacted with either hydroxylamine hydrochloride and a base, free hydroxylamine in methanol or hydroxylamine and an organic acid (See, e.g., U.S. Pat. No. 5,274,085, the disclosure of which is incorporated herein by reference).

The 9-oxime erythromycin A derivative is converted into a 9-O-protected oxime by reacting it with an agent of the formula $R^1$-X, where $R^1$ is a protecting group such as an alkyl substituted or unsubstituted cyclohexyl (e.g., isopropylcyclohexyl), a lower alkenyl (e.g. an allyl group and the like), an aryl substituted methyl group (e.g., a benzyl group, a p-methoxybenzyl group, a p-chlorobenzyl group, a m-chlorobenzyl group, an o-chlorobenzyl group, a 2,4-dichlorobenzyl group, a p-bromobenzyl group, m-nitrobenzyl group, a p-nitrobenzyl group, a benzhydryl group, a trityl group, 1-naphthylmethyl group and the like), a substituted oxyalkyl group (e.g. a methoxymethyl group, a (2-methoxyethoxy) methyl group, a (2-ethoxyethoxy) methyl group, a (2-methylpropoxy) methyl group, a 2-chloroethoxymethyl group, a 2,2,2-trichloroethoxymethyl group, a 2-ethoxyethyl group, a benzyloxymethyl group, a p-chlorophenoxyethyl group and the like), a substituted alkyl group [e.g., a (1,3-dioxolan-2-yl) methyl group, 3,3-dimethyl-2-oxobutyl group and the like] or a substituted thiomethyl group (e.g., a methylthiomethyl group, an ethylthiomethyl group, a phenylthiomethyl group and like) and X is a halogen (e.g., chloride, bromide, iodide) or a sulfonate acid (e.g., mesylate, tosylate).

A 9-O-protected oxime erythromycin A derivative has the structure I, below:

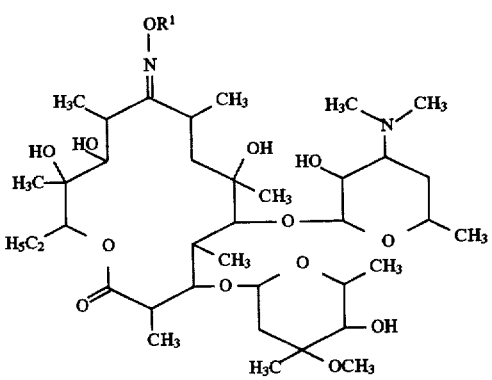

wherein

R¹ is selected from the group consisting of hydrogen, a lower alkenyl group, an aryl (lower alkyl) group, or a substituted aryl (lower alkyl) group, and

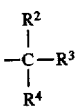

wherein

R² is selected from the group consisting of a lower alkyl group, a cycloalkyl group, a phenyl group, an aryl (lower alkyl) group; or R³ is selected from the group consisting of a lower alkyl group, a lower alkoxymethyl group; or R⁴ is selected from the group consisting of a hydrogen atom a lower alkyl group; a phenyl group an aryl (lower alkyl) group; or R² and R³, R² and R⁴ or R³ and R⁴ and the atoms to which they are attached are taken together to form a 5- to 7-membered ring containing one oxygen atom; or R⁴ and R³ and the atoms to which they are attached are taken together to form a 5- to 7-membered cycloalkyl group; with the requirement that only one pair of substituents (R² and R³), (R² and R⁴) or (R³ and R⁴) may be taken together with the atoms to which they are attached to form a ring as defined above.

The compound of structure I is shown without spatial bond orientation. Structure I, thus, defines all combinations of bond orientation and is intended to cover all possible stereo-configurations (e.g., epimers). In a preferred embodiment, the bond orientations of Structure I are the same as shown above for 6-O-methylerythromycin A.

As is well known in the art, to efficiently and selectively alkylate erythromycin A at the 6-hydroxyl position, the hydroxyl group at the 2'-position should be O-protected prior to alkylation. O-protection of that hydroxyl group can be done at any time prior to alkylation. In a preferred embodiment, O-protection of the 2'-position occurs immediately prior to alkylation.

O-protection of the 2'-hydroxyl is accomplished using conventional O-protecting groups (See, e.g., U.S. Pat. No. 4,672,109). Exemplary and preferred such O-protecting groups are alkoxycarbonyl groups (e.g., a methoxycarbonyl group, an ethoxycarbonyl group, an isopropoxycarbonyl group, an n-propoxycarbonyl group, an n-butoxycarbonyl group, an isobutyloxycarbonyl group, a sec-butyloxycarbonyl group, a t-butyloxycarbonyl group, a 2-ethylhexyloxycarbonyl group, a cyclohexyloxycarbonyl group, a methyloxycarbonyl group and the like); alkoxy- alkoxycarbonyl groups (e.g., a methoxymethoxycarbonyl group, an ethoxymethoxycarbonyl group, a 2-methoxyethoxycarbonyl group, a 2-ethoxyethylcarbonyl group, a 2-ethoxyethoxycarbonyl group, a 2-butoxyethoxycarbonyl group, a 2-methoxyethoxymethoxycarbonyl group and the like); haloalkoxycarbonyl groups (e.g., a 2-chloroethoxycarbonyl group, a 2-chloroethoxycarbonyl group, a 2,2,2-trichloroethoxycarbonyl group and the like), unsaturated alkoxycarbonyl groups (e.g., an allyloxycarbonyl group, a propargyloxycarbonyl group, a 2-butenoxycarbonyl group, a 3-methyl-2-butenoxycarbonyl group and the like), substituted benzyloxycarbonyl groups (e.g., a benzyloxycarbonyl group, a p-methylbenzyloxycarbonyl group, a p-methoxybenzyloxycarbonyl group, a p-nitrobenzyloxycarbonyl group, a 2,4-dinitrobenzyloxycarbonyl group, a 3,5-dimethylbenzyloxycarbonyl group, a p-chlorobenzyloxycarbonyl group, a p-bromobenzyloxycarbonyl group and the like), and substituted phenoxycarbonyl groups (e.g., a phenoxycarbonyl group, a p-nitrophenoxycarbonyl group, an o-nitrophenoxycarbonyl group, a 2,4-dinitrophenoxycarbonyl group, a p-methylphenoxycarbonyl group, an m-methylphenoxycarbonyl group, an o-bromophenoxycarbonyl group, a 3,5-dimethylphenoxycarbonyl group, a p-chlorophenoxycarbonyl group, a 2-chloro-4-nitrophenoxycarbonyl group and the like), aroyl groups, acyl groups used in usual organic synthesis (e.g., lower alkyl monocarbonyl groups such as an acetyl group, a propionyl group, a butyryl group, an isobutyryl group and the like; lower alkenyl monocarbonyl groups such as an acryloxyl group, a methacryloxy group and the like; lower alkoxycarbonylalkylcarbonyl groups such as a methoxycarbonylmethylcarbonyl group, an ethoxycarbonylmethylcarbonyl group, an ethoxycarbonylethylcarbonyl group and the like; arylcarbonyl groups such as a benzoyl group, a p-methoxybenzoyl group, a 3,4,5-trimethoxybenzoyl group, a p-chlorobenzoyl group, a 2,4-dichlorobenzoyl group, a 3,5-dichlorobenzoyl group, a diphenylacetyl group, a 1-naphthaleneacetyl group, a 2-naphthaleneacetyl group and the like) (See, e.g., Greene and Wuts' *Protective Groups in Organic Synthesis*, 2d. Ed. John Wiley & Sons, Inc., New York, 1991., the disclosure of which is incorporated herein by reference).

The 2'-protected, 9-O-protected oxime derivative is prepared by treating a compound of structure I, above with the corresponding acyl halide (e.g., acyl chloride) or acid anhydride. O-protection of the 2'-hydroxyl results in formation of a 2'-protected, 9-O-protected oxime of the structure II, below:

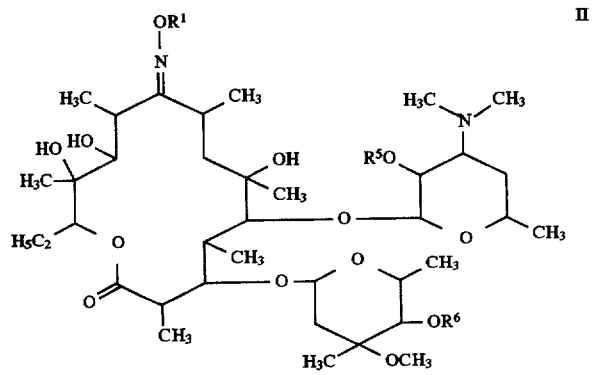

where $R^1$ is as defined above;

$R^5$ is alkoxycarbonyl, alkoxyalkoxy-carbonyl, haloalkoxycarbonyl, unsaturated alkoxycarbonyl, substituted benzyloxycarbonyl, substituted phenoxycarbonyl; and $R^6$ is hydrogen or $R^5$ as is defined above. Preferably, $R^5$ is arylcarbonyl or lower alkyl monocarbonyl. More preferably, $R^5$ is benzoyl or acetate.

The protection of the 2'-position is performed in the presence of a base and a solvent. Suitable bases are organic bases such as triethylamine, pyridine and diethylamine. An exemplary and preferred solvent is an organic solvent such as methylene chloride.

The compound of Structure II, above, is then selectively alkylated, usually methylated at the 6-position. Procedures and reagents for alkylating the 6-position of erythromycin A derivatives are well known in the art (See, e.g., U.S. Pat. Nos. 4,672,109 and 4,670,549).

Briefly, a compound of Structure II is reacted with a suitable alkylating agent in the presence of a base. Exemplary and preferred alkylating agents are methyl bromide, ethyl bromide, n-propyl bromide, methyl iodide, ethyl iodide, n-propyl bromide, dimethyl sulfate, diethyl sulfate, di-n-propyl sulfate, methyl-p-toluenesulfonate, ethyl methanesulfonate, and n-propyl methanesulfonate.

Exemplary and preferred bases are a strong alkali metal base, preferably selected from the group consisting of an alkali metal hydride, alkali metal hydroxide or alkali metal alkoxide, and a weak organic amine base, preferably selected from the group consisting of trimethylamine, triethylamine, tripropylamine, pyridine, 2-methoxypyridine, 1-methylpyrrolidine, 1-methylpiperidine, and 1-ethylpiperidine.

The methylation step is carried out in a suitable solvent that includes methyl-t-butyl ether. Exemplary and preferred solvents are polar aprotic solvents such as N,N-dimethylformamide, dimethyl sulfoxide, N-methyl-2-pyrrolidone, hexamethylphosphoric triamide, tetrahydrofuran, 1,2-dimethoxyethane, acetonitrile or ethyl acetate, or a mixture of such polar aprotic solvents maintained at a reaction temperature and for a period of time sufficient to effect alkylation, preferably from −15° C. to room temperature for a period of 1 to 8 hours.

The formed 6-O-alkyl derivative has the structure III, below:

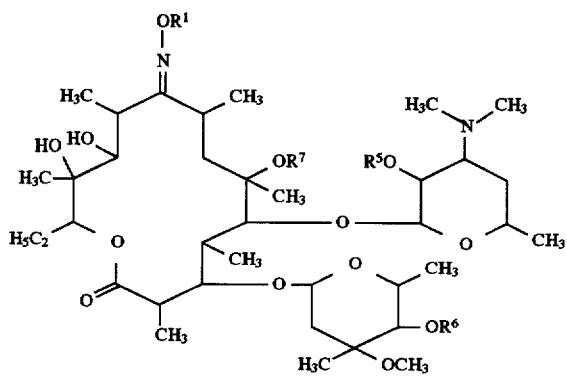

where $R^1$, $R^5$ and $R^6$ are as defined above, and $R^7$ is alkyl. Preferably, $R^7$ is lower alkyl and, more preferably a $C_1$–$C_4$ alkyl. The presence of methyl-t-butyl ether appears to inhibit and minimize the formation of the N-alkylated quaternary salt on the desosamine sugar, possibly by controlling and/or slowing the rate of alkylation.

The preparation of 6-O-alkyl-erythromycin A proceeds by removing the O-protecting groups from the 2'-position and from the 9-oxime and then deoximating the 9-oxime. Means for removing the protecting group at the 2'-position are well known in the art and depend upon the nature of the protecting group.

By way of example, where the 2'-position is acetylated, the acetyl group can be removed by reacting the acetylated derivative with an alkyl alcohol (e.g., methanol, ethanol, propanol, isopropanol, n-butanol, sec-butanol, t-butanol and the like). The reaction can take place in the absence or presence of an acid (e.g., formic acid, acetic acid), a base $(K_2CO_3, Na_2CO_3)$ or water.

Means for removing the O-protecting group at the 9-oxime position are well known in the art and depend upon the nature of the protecting group. By way of example, where the 9-O-protected oxime is a 9-oxime ketal (e.g., 9-oximeisopropylcyclohexyl ketal), deketalization is accomplished by treating the 9-oximeisopropylcyclohexyl ketal derivative with an acid in the presence of an alcohol. A preferred acid is an organic acid such as formic acid. A preferred alcohol is an alkyl alcohol such as methanol. Where the 9-O-protected oxime is a 9-oximehalobenzyl compound (e.g., 9-oxime-2-chlorobenzyl), debenzylation can be accomplished by reacting the 9-oximehalobenzyl compound with acid in alcohol in the presence of palladium.

A final step in the preparation of 6-O-alkylerythromycin A is deoximation. Deoximation is carried out in accordance with standard procedures well known in the art (See e.g., U.S. Pat. No. 4,672,109). Briefly, the 9-oxime derivative is reacted with sodium hydrogen sulfite in alcohol (e.g., ethanol) and refluxed. The solution is cooled, alkalinized and precipitated with aqueous sodium bicarbonate. The precipitate formed in the above reaction is collected by filtration, washed and recrystallized with alcohol.

Detailed descriptions of the synthesis of 6-O-methyl-erythromycin A, using a process of the present invention are set forth hereinafter in the Examples. Schematic illustrations of four embodiments of a synthetic scheme in accordance with the present invention are set forth in FIGS. 1, 2, 3 and 4.

With reference to FIG. 1, a 9-oximeisopropylcyclohexyl ketal erythromycin A derivative (Compound 1-1) is reacted with acetic anhydride ($Ac_2O$) in the presence of dichloromethane ($CH_2Cl_2$) and pyridine to form a 2'-acetyl (AcO), 9-oximeisopropylcyclohexyl ketal erythromycin A derivative (Compound 1-2).

Compound 1-2 is then reacted with a methylating agent (MeX) and potassium hydroxide (KOH) in an appropriate solvent [dimethylsulfoxide (DMSO) THF] in the presence of methyl-t-butyl ether (MTBE) to form a 2'-acetyl, 6-O-methyl, 9-oximeisopropylcyclohexyl ketal erythromycin A derivative (Compound 1-3).

The ketal group at the 9-position and the acetyl group at the 2'-position are removed by reacting Compound 1-3 with formic acid in alcohol to form a 2'—OH, 6-O-methyl, 9-oxime erythromycin A derivative (Compound 1-4). Compound 1-4 is then deoximated to yield 6-O-methylerythromycin A (clarithromycin).

Figure 2:
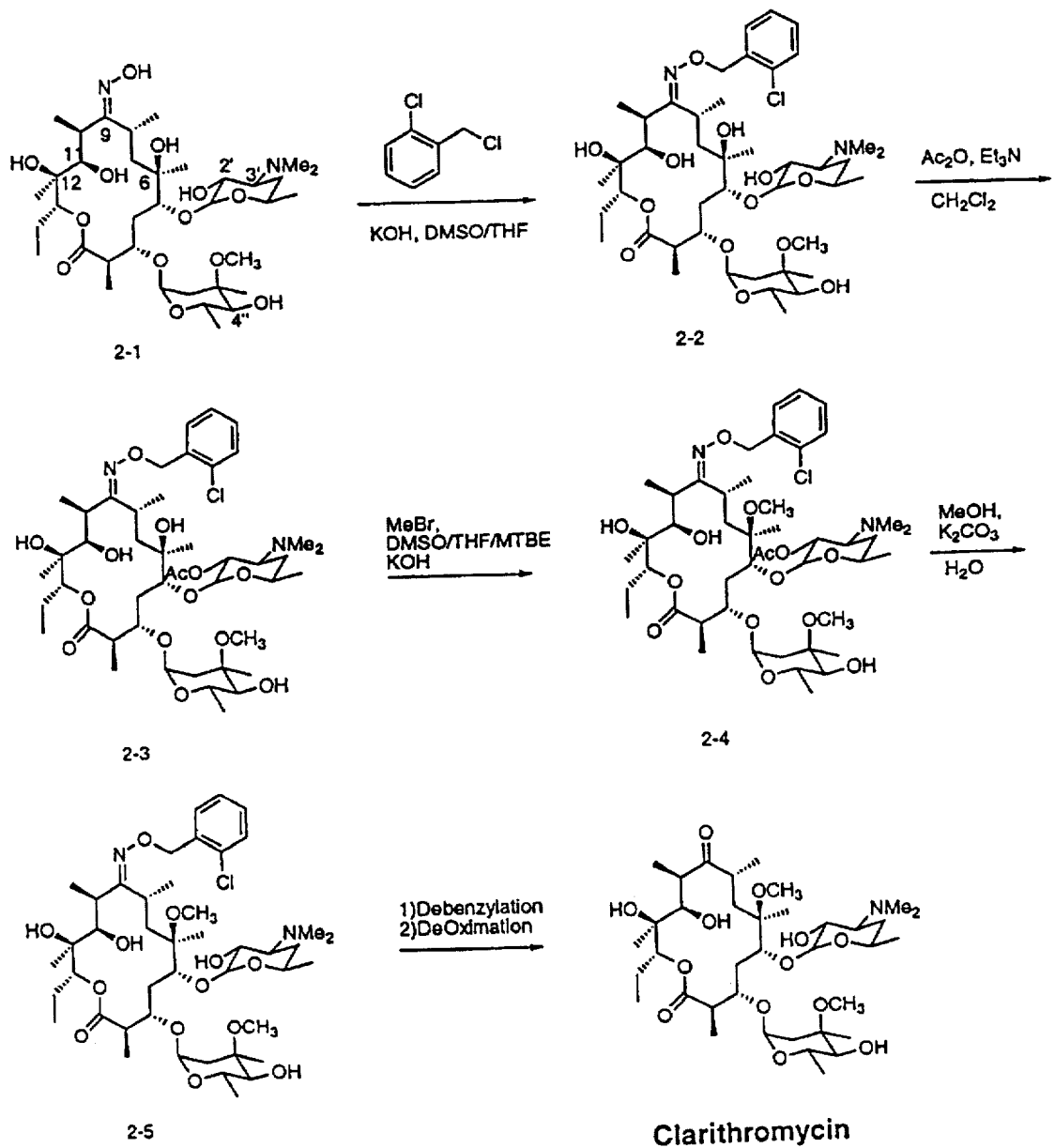
FIG. 2 shows a second embodiment of a process of preparing 6-O-methyl erythromycin A using a 2-chloro benzyl protecting group on the 9-oxime and an acetyl protecting group on the 2'—OH.

With reference to FIG. 2, a 2'—OH, 9-oxime erythromycin A derivative (Compound 2-1) is reacted with 2-chlorobenzyl chloride and potassium hydroxide (KOH) in the presence of dimethylsulfoxide (DMSO) and tetrahydrofuran (THF) to form a 9-oxime-2-chlorobenzyl erythromycin A derivative (Compound 2-2).

Compound 2-2 is then reacted with acetic anhydride ($Ac_2O$) in the presence of dichloromethane ($CH_2Cl_2$) and a pyridine to form a 2'-acetyl (AcO), 6—OH, 9-oxime-2-chlorobenzyl erythromycin A derivative (Compound 2-3).

Compound 2-3 is then reacted with methylbromide (MeBr) and potassium hydroxide (KOH)in an appropriate solvent [DMSO, THF] and methyl-t-butyl ether (MTBE) to form a 2'-acetyl, 6-O-methyl, 9-oxime-2-chlorobenzyl erythromycin A derivative (Compound 2-4).

The acetyl group at the 2'-position is removed by reacting Compound 2-4 with methanol (MeOH) in water to form a 6-O-methyl, 9-oxime-2-chlorobenzyl erythromycin A derivative (Compound 2-5). Compound 2-5 is then debenzylated and deoximated to yield 6-O-methyl erythromycin A (clarithromycin).

Figure 3:
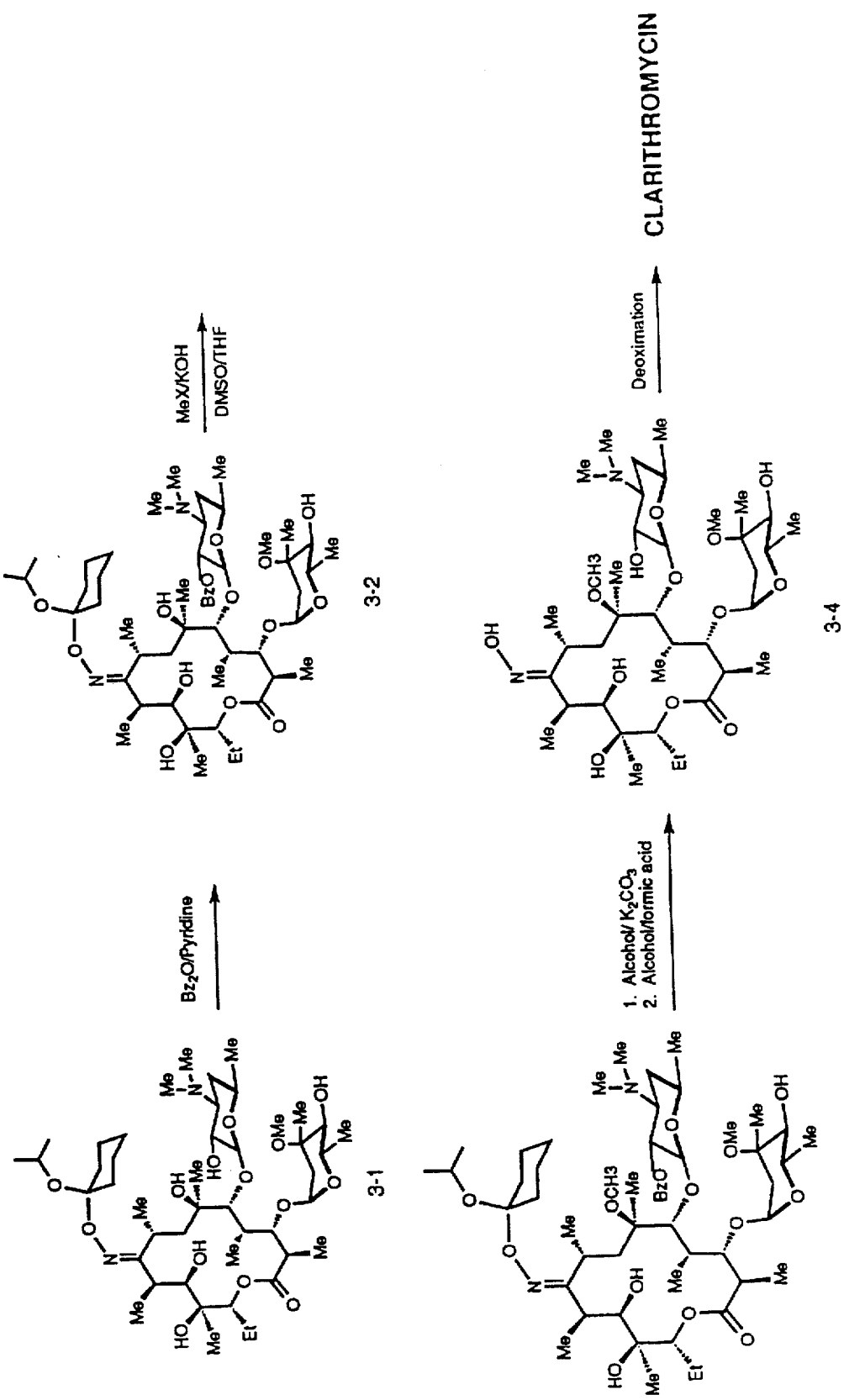
FIG. 3 shows a third embodiment of a process of preparing 6-O-methyl erythromycin A using a cyclohexyl ketal protecting group on the 9-oxime and a benzoyl protecting group on the 2'—OH.

With reference to FIG. 3, a 9-ketal oxime erythromycin A derivative (Compound 3-1) is reacted with benzoic anhydride (Bz$_2$O) in the presence of pyridine to form a 2'-benzoyl, 9-ketal oxime erythromycin A derivative (Compound 3-2).

Compound 3-2 is then reacted with a methylating agent (MeX) and potassium hydroxide (KOH) in an appropriate solvent [dimethylsulphoxide (DMSO) THF] in the presence of methyl-t-butyl-ether to form a 2'-benzoyl, 6-O-methyl, 9-ketal oxime erythromycin A derivative (Compound 3-3). The benzoyl group at the 2'-position of compound 3-3 is removed by reacting Compound 3-3 with alcohol/K$_2$CO$_3$ floowed by alcohol/and formic acid to form a 6-O-methyl, 9-oxime erythromycin A derivative (Compound 3-4).

Compound 3-4 is then deoximated to yield 6-O-methyl erythromycin A (clarithromycin).

Figure 4:
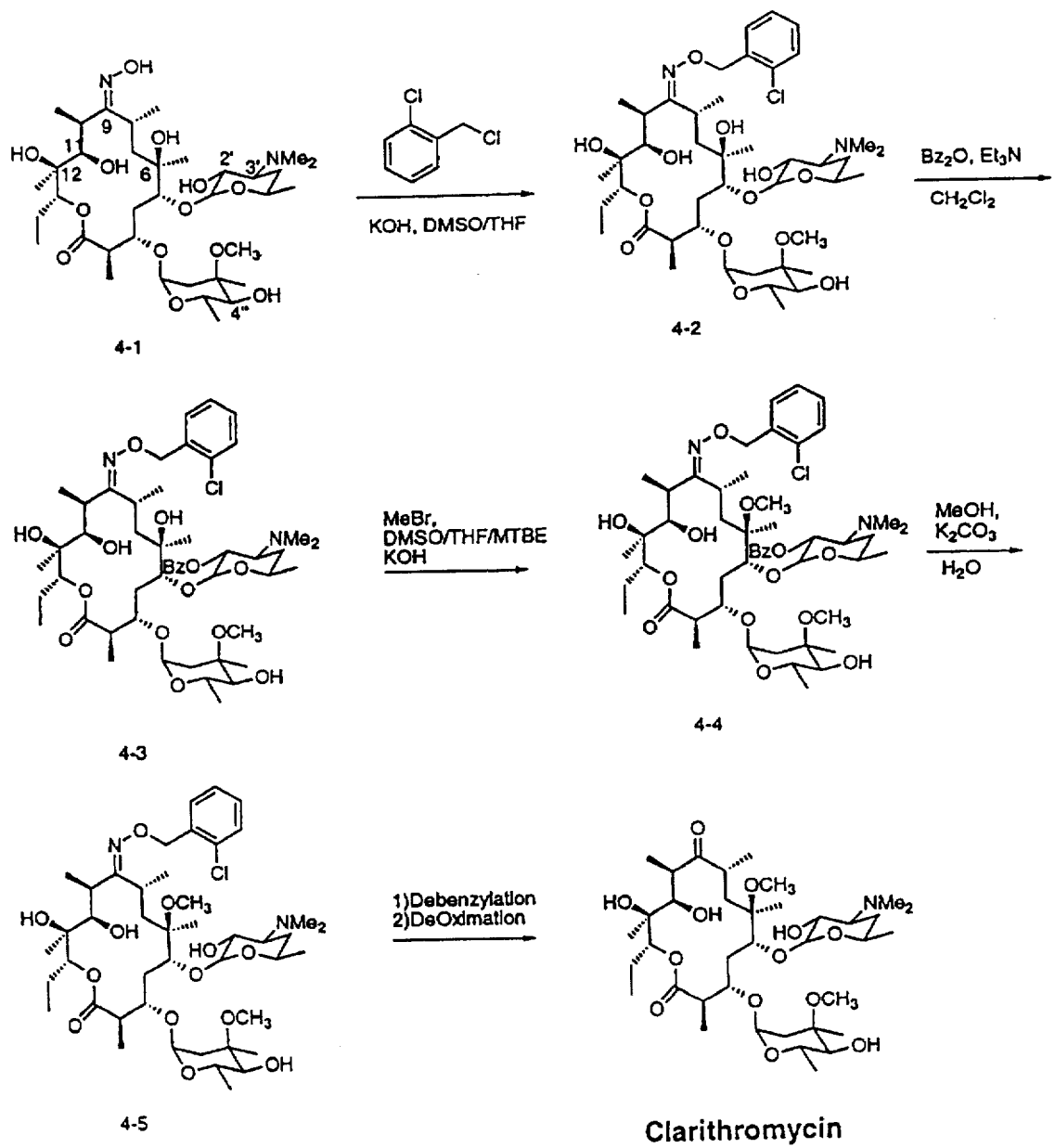
FIG. 4 shows a fourth embodiment of a process of preparing 6-O-methyl erythromycin A using a 2-chloro benzyl protecting group on the 9-oxime and a benzoyl protecting group on the 2'—OH.

With reference to FIG. 4, a 9-oxime erythromycin A derivative (Compound 4-1) is reacted with 2-chlorobenzyl chloride and potassium hydroxide (KOH) in the presence of dimethylsulfoxide (DMSO) and tetrahydrofuran (THF) to form a 9-oxime-2-chlorobenzyl erythromycin A derivative (Compound 4-2).

Compound 4-2 is then reacted with benzoic anhydride (Bz$_2$O) in the presence of dichloromethane (CH$_2$Cl$_2$) and a triethylamine (Et$_3$N) to form a 2'-benzoate, 9-oxime-2-chlorobenzyl erythromycin A derivative (Compound 4-3).

Compound 4-3 is then reacted with methylbromide (MeBr) and potassium hydroxide (KOH) in an appropriate solvent [DMSO, THF and methyl-t-butyl ether (MTBE)] to form a 2'-benzoate, 6-O-methyl, 9-oxime-2-chlorobenzyl erythromycin A derivative (Compound 4-4).

The benzoyl group at the 2'-position is removed by reacting Compound 4-4 with methanol (MeOH) and potassium carbonate (K$_2$CO$_3$) in water to form a 6-O-methyl, 9-oxime-2-chlorobenzyl erythromycin A derivative (Compound 4-5). Compound 4-5 is then debenzylated and deoximated to yield 6-O-methyl erythromycin A (clarithromycin).

The present invention also provides 2'-protected, 3'-dimethylamine, 9-O-protected oxime derivatives of erythromycin A, which derivatives are intermediates in the synthesis of 6-O-alkyl erythromycin A. Such a derivative of the present invention can be alkylated at the 6'-position (i.e., 6-O-alkyl). Thus, a 9-O-protected oxime erythromycin A derivative of the present invention corresponds to the structure IV, below.

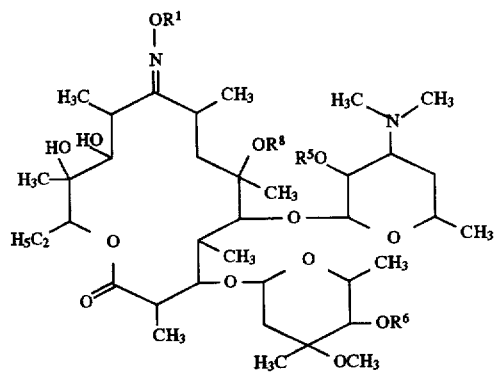

where R$^1$, R$^5$ and R$^6$ are as defined above, and R$^8$ is hydrogen or alkyl. Preferably the alkyl is a lower alkyl and, more preferably, a C$_1$–C$_4$ alkyl.

The following Examples illustrate preferred embodiments of the present invention and are not limiting of the specification and claims in any way.

EXAMPLE 1

Preparation Of 2' Acetyl Erythromycin A Oxime IPCH Ketal

A mixture of erythromycin A oxime isopropylcyclohexyl (IPCH) ketal (20 grams, 22.5 mmol), Ac$_2$O (20 ml) and pyridine (35 ml) in methylene chloride (150 ml) was stirred at room temperature for 3 hours and quenched with water (100 ml). The resulting mixture was poured into t-butyl methyl ether/saturated brine (500 ml/150 ml). The organic layer was washed with saturated brine dried over MgSO$_4$, filtered and evaporated to dryness to provide 18 grams of 2' acetyl erythromycin A oxime IPCH ketal as a solid. $^1$H NMR δ: 1.45 (3H, 6—CH$_3$), 3.65 (1H, 11—OH), 1.14 (3H, 12—CH$_3$), 2.07 (3H, 2'—Ac), 2.31 (6H, N—(CH$_3$)$_2$), 3.36 (3H, 3"—OCH$_3$); $^{13}$C NMR δ: 67.2 (6—C), 70.6 (11—C), 74.1 (12—C), 170.0 (2'—C=O), 63.6 (3"—CH), 77.9 (4"—CH), 49.4 (3"—OCH$_3$), 169.8 (9—C). MS (Cl) m/z 930.

EXAMPLE 2

Preparation Of 2' Acetyl 6-O-Methyl Erythromycin A Oxime IPCH Ketal

A solution of 2' acetyl erythromycin A oxime IPCH ketal (5.0 grams, 5.4 mmol) in tetrahydrofuran (20 ml) and dimethylsulfoxide (30 ml) was cooled to 0°–5° C. and a solution of 2 M methyl bromide in t-butyl methyl ether (20 ml, 40 mmol) was added. Powdered potassium hydroxide (1.2 grams, 21 mmol) was then added. The resulting mixture was stirred for 1.5 hours and then quenched with an aqueous methylamine solution (5 ml). The mixture was stirred at room temperature for 15 minutes and then extracted with t-butyl methyl ether (350 ml). The organic layer was washed with water (2×50 ml) and saturated brine (50 ml) and dried over MgSO$_4$. The solvent was removed under vacuum to yield 4.2 grams of 2' acetyl 6-O-methyl erythromycin A oxime IPCH ketal as a glassy solid. $^1$H NMR δ: 1.41 (3H, 6—CH$_3$), 3.08 (3H, 6—OCH$_3$), 3.71 (1 H, 11—CH), 2.06 (3H, 2'—Ac), 2.32 (6H, N—CH$_3$)$_2$), 3.05.(1H, 4"—CH); $^{13}$C NMR δ: 68.7 (6—C), 70.1 (11—C), 170.0 (2'—C=O), 63.6 (3'—CH), 77.8 (4"—CH). MS (Cl) m/z 944.

EXAMPLE 3

Preparation Of 6-O-Methyl Erythromycin A Oxime IPCH

A solution of 2' acetyl 6-O-methyl erythromycin A oxime IPCH ketal (2.6 grams, 2.2 mmol) in methanol (100 ml) and water (20 ml) was stirred at room temperature for 58 hours. The solution was poured into 300 ml of methyl t-butyl ether. The organic layer was washed with brine and dried over MgSO$_4$. The solvent was removed under vacuum to yield 2.4 grams of 6-O-methyl erythromycin A oxime IPCH. $^1$H NMR δ: 1.45 (3H, 6—CH$_3$), 3.11 (3H, 6—OCH$_3$), 3.20 (1H, 2'—CH), 2.30 (6H, N—(CH$_3$)$_2$); $^{13}$C NMR δ: 78.7 (6—C), 51.2 (6—OCH$_3$), 169.8 (9—C), 71.1 (2'—CH). MS (CI) m/z 902.

EXAMPLE 4

Preparation Of Clarithromycin From 2' Acetyl Erythromycin A Oxime IPCH Ketal

2' Acetyl erythromycin A oxime IPCH ketal, (1.37 grams, 1.46 mmole) was dissolved in 12.5 ml of THF and 12.5 ml of DMSO. The solution was cooled to 0°–5° C. and 1.8 grams (17.8 mmole) of triethylamine and 1.75 grams (18.4 mmole) of methyl bromide were added. Powdered KOH (0.3 grams, 4.3 mmole) was then added. The mixture was stirred for 9 minutes and then quenched with 50 ml of heptane and 10 ml of 2N NaOH. The layers were separated and the solvent was removed to yield 1.04 grams of methylated product. The solid was dissolved in 30 ml of methanol and 8 ml of a 5% potassium carbonate solution. The mixture was stirred at room temperature overnight and extracted with 50 ml of isopropyl acetate. The organic phase was dried with magnesium sulfate and the solids were removed by filtration. The solvent was stripped under vacuum, providing 0.9 grams of diacetyl product.

This diacetyl product was dissolved in 60 ml of 3A alcohol and 60 ml of water. Thirteen drops of formic acid were added and the solution was heated to 60°–65° C. for 4 hours. Three grams of sodium bisulfite were added and the reaction was heated for another 4 hours. The solution was cooled to room temperature and then stripped under vacuum until precipitates appeared. The heterogeneous mixture was extracted with 100 ml isopropyl acetate. After separating the layers, the organic phase was dried with magnesium sulfate, filtered, and the solvent removed to produce 0.41 grams of clarithromycin. Re-isolation of the aqueous solution with methylene chloride provided another 0.2 grams of clarithromycin.

EXAMPLE 5

Preparation Of Erythromycin A 9-[O-(2-Chlorobenzyl) Oxime]

A solution of erythromycin A 9-oxime (15 grams) in dimethylsulfoxide (25 ml) and tetrahydrofuran (25 ml) was cooled to 5° C. To this solution, 2-chlorobenzyl chloride (3.2 grams) and 85% potassium hydroxide powder (1.5 grams) were added. The mixture was stirred at 5°–10° C. for 3 hours. A forty percent aqueous methylamine solution (5 ml) and water (50 ml) were added. The mixture was extracted with isopropyl acetate (200 ml). The organic layer was washed with water (2×100 ml) and dried over MgSO$_4$. The solvent was evaporated in vacuo to dryness and the white solid product was triturated with heptane, filtered and dried to provide 11 grams of product. $^1$H NMR (CDCl$_3$, 500 MHz) δ: 2.28 (s, 6H, —N(CH$_3$)$_2$), 3.31 (s, 3H, 3"—OCH$_3$), 5.16 (S, 2 H, OCH$_2$); $^{13}$C NMR (CDCl$_3$) δ: 40.2 (—N(CH$_3$)$_2$), 49.4 (3"—OCH$_3$), 73.0 (—OCH$_2$). MS (CI, MH$^+$) m/z 872.

EXAMPLE 6

Preparation Of Erythromycin A 9-[O-(2-Chlorobenzyl) Oxime]-2'-Acetate

Pyridine (12 ml) and acetic anhydride (6 ml) were added to a solution of erythromycin A 9-[O-(2-Chlorobenzyl) oxime] (6 grams) in dichloromethane (60 ml). The reaction mixture was stirred at room temperature for 1 hour and water (100 ml) was added. The organic layer was separated and the aqueous layer extracted with methyl-t-butyl ether. The organic layers were combined, washed with water (100 ml) and dried over MgSO$_4$. The solvent was evaporated to dryness to provide 6 grams of product as a white solid. The product was recrystallized from isopropyl acetate. The product was characterized by $^1$H and $^{13}$C NMR. $^1$H NMR (CDCl$_3$, 300 MHz) δ: 2.05 (s, 3H, —COCH$_3$), 2.27 (s, 6H, —N(CH$_3$)$_2$), 3.35 (s, 3H, 3"—OCH$_3$), 5.17 (S, 2 H, —OCH$_2$). MS (CI, MH$^+$) m/z 915.

EXAMPLE 7

Preparation Of Erythromycin A 9-[O-(2-Chlorobenzyl) Oxime]-2'-Acetate-6-O-Methyl A solution of erythromycin A 9-[O-(2-Chlorobenzyl) oxime]-2'-acetate (5 grams) in dimethylsulfoxide (20 ml) and tetrahydrofuran (10 ml) was cooled to 3° C. A 2M solution of methyl bromide in methyl-t-butyl ether (20 ml) and 85% potassium hydroxide powder (1.1 grams) were added to this mixture. The mixture was stirred at 3°–5° C. for 5 hours. A forty percent aqueous methylamine solution (5 ml) and water (50 ml) were added. The mixture was extracted with methyl-t-butyl ether (500 ml). The organic layer was washed with water (2×100 ml) and dried over MgSO$_4$. The solvent was evaporated in vacuo to dryness to provide 4.9 grams of product as a white solid. MS (CI, MH$^+$) m/z 929.

EXAMPLE 8

Preparation Of Erythromycin A 9-[O-(2-Chlorobenzyl) Oxime]-6-O-Methyl

Erythromycin A 9-[O-(2-Chlorobenzyl) oxime]-2'-acetate-6-O-methyl (1.5 grams) was dissolved in methanol (12 ml) and water (2 ml). The mixture was stirred at room temperature for 50 hours. The solvent was evaporated in vacuo and the gummy residue was dissolved in methyl-t-butyl ether. The organic solution was washed with water, dried over MgSO$_4$ and evaporated to dryness to yield 1.5 grams of white solid. The product was recrystallized from methanol. The product was characterized $^1$H and $^{13}$C NMR. $^1$H NMR (CDCl$_3$, 500 MHz) δ: 2.30 (s, 6H, —N(CH$_3$)$_2$), 3.30 (s, 3 H, 6—OCH$_3$), 3.31 (s, 3H, 3"—OCH$_3$), 5.13 (S, 2 H. OCH$_2$); $^{13}$C NMR (CDCl$_3$) δ: 40.2 (—N(CH$_3$)$_2$), 49.4 (3"—O CH$_3$), 50.8 (6—OCH$_3$), 72.6 (—OCH$_2$). MS (CI, MH$^+$) m/z 887.

EXAMPLE 9

Preparation Of 2' Benzoyl Erythromycin A Oxime IPCH Ketal

A mixture of erythromycin A oxime IPCH ketal (27 grams, 22.5 mmol), Bz$_2$O (16 grams) and triethylamine (10 ml) in methylene chloride (90 ml) was stirred at room temperature for 60 hours and quenched with water (100 ml). The resulting mixture was poured into methylene chloride. The organic layer was washed with saturated aqueous NaHCO$_3$ and brine, dried over MgSO$_4$, filtered through silica gel (450 grams), eluted with 10% methanol in CH$_2$Cl$_2$ and evaporated to dryness to afford 26.3 grams of product as a white solid. 1H NMR δ: 1.47 (3H, 6—CH₃), 2.38 (6H, N—(CH₃)₂), 7.38 (t, 2H, Ph), 7.72 (d, 1H, Ph), 8.02 (d, 2H, Ph); ¹³C NMR (CDCl₃) δ: 40.3 (—N(CH₃)₂), 49.5 (3"—OCH₃), 75.2(6—C), 165.4 (2' PhCO). MS (CI) m/z 993, 853, 695, 262. MS (CI) m/z 993.

EXAMPLE 10

Preparation Of 2' Benzoyl 6-O-Methyl Erythromycin A Oxime IPCH Ketal

A solution of 2' benzoyl erythromycin A oxime IPCH ketal (5.0 grams, 5.0 mmol) in tetrahydrofuran (12 ml) and dimethylsulfoxide (18 ml) was cooled to 0°–5° C. A solution of 2 M methyl bromide in t-butyl methyl ether (16 ml, 32 mmol) and powdered potassium hydroxide (1.2 grams, 21 mmol) were added to the solution. The resulting mixture was stirred for 2.0 hours and then quenched with an aqueous methylamine solution (5 ml). The mixture was stirred at room temperature for 15 minutes and then extracted with t-butyl methyl ether (400 ml). The organic layer was washed with water (3×50 ml) and saturated brine (50 ml) and dried over MgSO₄. The solvent was removed under vacuum to yield 4.2 grams of 2' benzoyl 6-O-methyl erythromycin A oxime IPCH ketal as a white solid. MS (CI) m/z 1006.

EXAMPLE 11

Preparation Of 6-O-Methyl Erythromycin A Oxime IPCH

Twelve ml of a 10% aqueous K₂CO₃ solution was added to a solution of 2' benzoyl 6-O-methyl erythromycin A oxime IPCH ketal (2.0 grams, 2.2 mmol) in methanol (45 ml). The cloudy mixture was heated at 55°–60° C. for 48 hours and then cooled to room temperature. The solid was filtered, washed with water and dried under vacuum at 50° C. for 20 hours to give 1.2 grams of 6-O-methyl erythromycin A oxime IPCH. ¹³C NMR (CDCl₃) δ: 51.2 (6—OCH₃), 78.7 (6—C), 71.1 (2'—CH), 169.8 (9—C), 49.5 (3"—OCH₃), 75.2(6—C), 165.4 (2' PhCO). MS (CI) m/z 902, 763, 745, 605. MS (CI) m/z 902.

EXAMPLE 12

Erythromycin A 9-[O-(2-Chlorobenzyl) Oxime]-2'-Benzoate (3)

Benzoic anhydride (12.5 grams) and triethylamine (8 ml) were added to a solution of erythromycin A 9-[O-(2-Chlorobenzyl) oxime] (25 grams) in dichloromethane (100 ml). The reaction mixture was stirred at room temperature for 52 hours. The solvent was evaporated under vacuum and the residue dissolved in ethyl acetate. Water (100 ml) was added and the pH of the water layer was adjusted to a value of 13 using 50% NaOH. The organic layer was separated, washed with water (100 ml) and dried over MgSO₄. The solvent was evaporated to dryness to yield 23 grams of product as a white solid. The product was recrystallized from ethyl acetate. The product was characterized by ¹H and ¹³C NMR. ¹H NMR (CDCl₃, 500 MHz) δ: 2.26 (s, 6H, —N(CH₃)₂), 3.41 (s, 3H, 3"—OCH₃), 5.15 (S, 2 H, OCH₂); ¹³C NMR (CDCl₃) δ: 40.7 (—N(CH₃)₂), 49.4 (3"—OCH₃), 73.0 (—OCH₂), 175.2 (C=O). MS (CI, MH⁺) m/z 977.

EXAMPLE 13

Erythromycin A 9-[O-(2-Chlorobenzyl) Oxime]-2'-Benzoate-6-O-Methyl (4)

A solution of erythromycin A 9-[O-(2-Chlorobenzyl) oxime]-2'-benzoate (7 grams) in dimethylsulfoxide (35 ml) and tetrahydrofuran (35 ml) was cooled to 3° C. A 2M solution of methyl bromide in methyl-t-butyl ether (35 ml) and 85% potassium hydroxide powder (1.4 grams) were added to this mixture. The mixture was stirred at 3°–5° C. for 6.5 hours. A forty percent aqueous methylamine solution (5 ml) and water (50 ml) were added. The mixture was extracted with methyl-t-butyl ether (2×200 ml). The organic layer was washed with water (2×100 ml) and dried over MgSO₄. The solvent was evaporated in vacuo to dryness to give 6.4 grams of product as a white solid. MS (CI, MH⁺) m/z 991.

EXAMPLE 14

Erythromycin A 9-[O-(2-Chlorobenzyl) Oxime]-6-O-Methyl (5)

Erythromycin A 9-[O-(2-Chlorobenzyl) oxime]-2'-benzoate-6-O-methyl (4, 1.0 grams) was dissolved in methanol (25 ml) and water (7 ml). K₂CO₃ (700 mg) was then added. The mixture was stirred at 55°–60° C. for 48 hours. The mixture was cooled to room temperature and the solid product was filtered, washed with 50% aqueous methanol (10 ml) and dried to yield 300 mg of white solid. ¹³C NMR (CDCl₃) δ: 40.3 (—N(CH₃)₂), 49.5 (3"—OCH₃), 50.8 (6—OCH₃), 72.7 (—OCH₂). MS (CI, MH⁺) m/z 887.

What is claimed is:

1. A process of preparing a 6-O-alkyl-erythromycin A comprising:

protecting the 2'-hydroxyl position of a 9-O-protected oxime derivative of erythromycin A with an alkoxycarbonyl, alkoxyalkoxy-carbonyl, haloalkoxycarbonyl, unsaturated alkoxycarbonyl, substituted benzyloxycarbonyl, substituted phenoxycarbonyl, acyl or aroyl protecting group to form a 2'-protected, 9-O-protected oxime derivative of erythromycin A;

reacting the 2'-protected derivative with an alkylating agent in the presence of methyl-t-butyl ether; and deprotecting the 9- and 2'-positions to give 6-O-alkyl erythromycin A.

2. The process of claim 1 wherein the protecting group at the 2'-position is arylcarbonyl or lower alkyl monocarbonyl.

3. The process of claim 2 wherein the arylcarbonyl is benzoyl.

4. The process of claim 2 wherein the lower alkyl monocarbonyl is acetyl.

5. The process of claim 1 wherein the 9-O-protected oxime erythromycin A derivative is a 9-O-halobenzyl oxime or a 9-O-alkylcyclohexyl oxime erythromycin A derivative.

6. The process of claim 5 wherein 9-O-halobenzyl oxime erythromycin A derivative is 9-O-2-chlorobenzyl oxime erythromycin A.

7. The process of claim 5 wherein the 9-O-alkylcyclohexyl oxime erythromycin A derivative is 9-oximeisopropylcyclohexyl ketal erythromycin A.

8. A compound of the structure below:

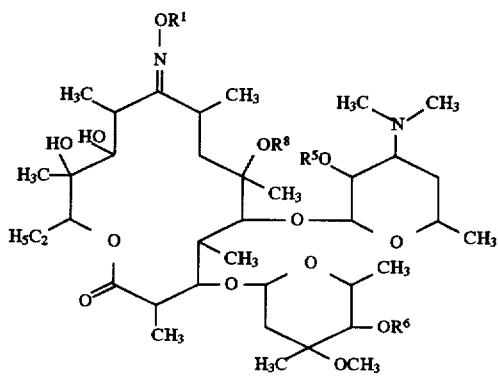

IV wherein:

$R^1$ is selected from the group consisting of hydrogen, a lower alkenyl group, an aryl (lower alkyl) group, a substituted aryl (lower alkyl) group, and

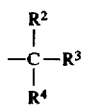

wherein $R^2$ is selected from the group consisting of a lower alkyl group, a cycloalkyl group, a phenyl group, and an aryl (lower alkyl) group;

$R^3$ is selected from the group consisting of a lower alkyl group, and a lower alkoxymethyl group; and $R^4$ is selected from the group consisting of a hydrogen atom, a lower alkyl group; a phenyl group and an aryl (lower alkyl) group; or $R^2$ and $R^3$, $R^2$ and $R^4$ or $R^3$ and $R^4$ and the atoms to which they are attached are taken together to form a 5- to 7-membered ring containing one oxygen atom; or $R^4$ and $R^3$ and the atoms to which they are attached are taken together to form a 5- to 7-membered cycloalkyl group; with the requirement that only one pair of substituents ($R^2$ and $R^3$), ($R^2$ and $R^4$) or ($R^3$ and $R^4$) may be taken together with the atoms to which they are attached to form a ring as defined above;

$R^5$ is alkoxycarbonyl, alkoxyalkoxy-carbonyl, haloalkoxycarbonyl, unsaturated alkoxycarbonyl, substituted benzyloxycarbonyl, substituted phenoxycarbonyl or alkylcarbonyl or arylcarbonyl;

$R^6$ is hydrogen or $R^5$; and $R^8$ is hydrogen or alkyl.

9. The compound of claim 8 wherein $R^8$ is hydrogen.

10. The compound of claim 8 wherein $R^8$ is methyl.

11. A method of inhibiting the formation of quaternary ammonium salts in the preparation of 6-O-alkyl-erythromycin A compounds, comprising:

reacting a protected erythromycin A compound with an alkylating agent in the presence of methyl-t-butyl ether, wherein said protected erythromycin A compound comprises at least a 9-oxime protection group and a 2'-hydroxyl protecting group selected from the group consisting of alkoxycarbonyl, alkoxyalkoxy-carbonyl, haloalkoxycarbonyl, unsaturated alkoxycarbonyl, substituted benzyloxycarbonyl, substituted phenoxycarbonyl, acyl and aroyl; and deprotecting the 9- and 2'-positions to give 6-O-alkyl erythromycin A.

12. The method according to claim 11 wherein the inhibition of quaternary ammonium salts formation is effected by controlling the rate of the alkylation reaction.

13. The method according to claim 11 wherein the alkylating agent is a methylating agent.

* * * * *